US012594078B2

(12) United States Patent
Chen et al.

(10) Patent No.: US 12,594,078 B2
(45) Date of Patent: Apr. 7, 2026

(54) VASO-OCCLUSIVE DEVICES

(71) Applicants: STRYKER CORPORATION, Kalamazoo, MI (US); STRYKER EUROPEAN OPERATIONS LIMITED, Carrigtwohill (IE)

(72) Inventors: Hancun Chen, San Ramon, CA (US); Andrew S. Lee, San Jose, CA (US)

(73) Assignees: Stryker Corporation, Kalamazoo, MI (US); Stryker European Operations Limited, Carrigtwohill (IE)

( * ) Notice: Subject to any disclaimer, the term of this patent is extended or adjusted under 35 U.S.C. 154(b) by 291 days.

(21) Appl. No.: 17/846,774

(22) Filed: Jun. 22, 2022

(65) Prior Publication Data

US 2022/0370078 A1 Nov. 24, 2022

Related U.S. Application Data

(63) Continuation of application No. PCT/US2021/057134, filed on Oct. 28, 2021.

(60) Provisional application No. 63/191,918, filed on May 21, 2021.

(51) Int. Cl.
*A61B 17/12* (2006.01)

(52) U.S. Cl.
CPC .... *A61B 17/12113* (2013.01); *A61B 17/1215* (2013.01); *A61B 17/12172* (2013.01); *A61B 2017/12063* (2013.01)

(58) Field of Classification Search
CPC .......... A61B 17/12113; A61B 17/1215; A61B 17/12172; A61B 2017/12063; A61B 2017/1205; A61B 2090/3966; A61B 17/1214; A61B 17/12145;
(Continued)

(56) References Cited

U.S. PATENT DOCUMENTS

| | | | | |
|---|---|---|---|---|
| 5,749,894 A | * | 5/1998 | Engelson | ......... A61B 17/12145 606/191 |
| 6,322,576 B1 | * | 11/2001 | Wallace | ........... A61B 17/12113 606/198 |

(Continued)

FOREIGN PATENT DOCUMENTS

| | | |
|---|---|---|
| WO | WO 2021/050710 A2 | 3/2021 |
| WO | WO 2021/050710 A3 | 4/2021 |

OTHER PUBLICATIONS

Https://metalcutting.com/wp-content/uploads/2018/06/Biomedical-Materials-Whitepaper_MetalCutting.pdf (Year: 2018).*
(Continued)

*Primary Examiner* — Andrew Restaino
(74) *Attorney, Agent, or Firm* — Vista IP Law Group, LLP

(57) ABSTRACT

A vaso-occlusive device, includes: a vaso-occlusive structure configured for implantation in an aneurysm sac, the vaso-occlusive structure having a delivery configuration when restrained within a delivery catheter and having a deployed configuration when released from the delivery catheter into the aneurysmal sac, at least a portion of the vaso-occlusive structure being composed of a AuPtW (gold-platinum-tungsten) alloy; wherein the AuPtW alloy comprises platinum within a range between 25% and 40% by weight, and wherein the AuPtW alloy comprises tungsten within a range between 0.01% and 10% by weight.

20 Claims, 7 Drawing Sheets

(58) Field of Classification Search
CPC .... A61B 17/12154; A61B 2017/00526; A61B
2017/12054; A61B 2017/12068
See application file for complete search history.

(56) References Cited

U.S. PATENT DOCUMENTS

| | | | | |
|---|---|---|---|---|
| 2007/0067009 | A1* | 3/2007 | Gandhi | A61F 2/915 |
| | | | | 623/1.34 |
| 2012/0226304 | A1* | 9/2012 | Ryan | A61B 17/12145 |
| | | | | 606/200 |
| 2014/0277099 | A1* | 9/2014 | Wallace | A61B 17/12031 |
| | | | | 606/200 |
| 2015/0025562 | A1* | 1/2015 | Dinh | A61M 25/0045 |
| | | | | 264/238 |
| 2017/0189035 | A1* | 7/2017 | Porter | A61B 17/12172 |
| 2019/0030215 | A1* | 1/2019 | Okubo | B21F 3/00 |
| 2019/0046684 | A1* | 2/2019 | Roth | A61L 27/54 |
| 2020/0170647 | A1 | 6/2020 | Chen et al. | |

OTHER PUBLICATIONS

Https://en.wikipedia.org/wiki/Young%27s_modulus.*
TWPinternationalpol. (Oct. 24, 2016). Low frictional resistance of
PTFE: A benefit in bridge bearing design. https://ipolymer.com/
blog/low-frictional-resistance-of-ptfe-a-benefit-in-bridge-bearing (Year:
2016).*
Notice of Rejection for JP Patent Appln. No. 2023-571528 dated
Jun. 3, 2025 (with English translation).
PCT International Search Report and Written Opinion for International Appln. No. PCT/US2021/057134, Applicant Stryker Corporation, dated Feb. 8, 2022 13 pages.
Extended European Search Report for EP Patent Appln. No. 25211370.9
dated Jan. 19, 2026.

* cited by examiner

VASO-OCCLUSIVE DEVICES

RELATED APPLICATION DATA

This application is a continuation of International Patent Application No. PCT/US2021/057134 filed on Oct. 28, 2021, which claims priority to and the benefit of U.S. Provisional Patent Application No. 63/191,918 filed on May 21, 2021, lapsed. The entire disclosures of the above applications are expressly incorporated by reference herein.

FIELD

The present disclosure relates generally to medical devices and intravascular medical procedures and, more particularly, to devices and methods for occluding vascular defects, such as aneurysms.

BACKGROUND

Vaso-occlusive devices or implants are used for a wide variety of reasons, including treatment of intra-vascular aneurysms. An aneurysm is a dilation of a vessel, such as a blood vessel, that may pose a risk to a patient's health due to rupture, clotting, or dissection. For example, rupture of an aneurysm in a patient's brain may cause a stroke, and lead to brain damage and death. Cerebral aneurysms may be detected in a patient, e.g., following seizure or hemorrhage, and may be treated by applying vaso-occlusive devices.

Commonly used vaso-occlusive devices include soft, helically wound coils formed by winding a platinum (or platinum alloy) wire strand about a "primary" mandrel.

The coil is then wrapped around a larger, "secondary" mandrel, and heat treated to impart a secondary shape. For example, U.S. Pat. No. 4,994,069, issued to Ritchart et al., which is fully incorporated herein by reference as though set forth in full, describes a vaso-occlusive device that assumes a linear, helical primary shape when stretched for placement through the lumen of a delivery catheter, and a folded, convoluted secondary shape when released from the delivery catheter and deposited in the vasculature. In order to better frame and fill aneurysms, complex three-dimensional secondary shapes can be imparted on vaso-occlusive devices and the stiffness/flexibility of vaso-occlusive devices can be modified.

In order to deliver the vaso-occlusive devices to a site in the vasculature, e.g., within an aneurysmal sac, it is well-known to first position a small profile delivery catheter or "micro-catheter" at the site using a guidewire. Typically, the distal end of the micro-catheter is provided, either by the attending physician or by the manufacturer, with a selected pre-shaped bend, e.g., 45 degrees, 26 degrees, "J", "S", or other bending shape, depending on the particular anatomy of the patient, so that it will stay in a certain position for releasing one or more vaso-occlusive device(s) into the aneurysmal sac once the guidewire is withdrawn. A delivery or "pusher" assembly or "wire" is then passed through the micro-catheter until a vaso-occlusive device coupled to a distal end of the delivery assembly is extended out of the distal end opening of the micro-catheter and into the aneurysmal sac. Once in the aneurysmal sac, portions of the vaso-occlusive device may deform or bend to allow more efficient and complete packing.

The vaso-occlusive device is then released or "detached" from the distal end of the delivery assembly, and the delivery assembly is withdrawn back through the micro-catheter. Depending on the particular needs of the patient, one or more additional vaso-occlusive devices may be pushed through the micro-catheter and released into the same aneurysmal sac.

Fluoroscopy is typically used to visualize vaso-occlusive devices during delivery into an aneurysm, while magnetic resonance imaging (MRI) may be used to visualize the treatment site post-procedure (e.g., a few weeks after initial treatment of the aneurysm) to ensure that the aneurysmal sac is properly occluded. As such, vaso-occlusive devices may be constructed in a manner that enables their radiopacity during treatment of the aneurysm, while minimizing any visualization obscuring artifacts created during the post-procedure MRI (i.e., being MRI-compatible). It is also paramount that such vaso-occlusive devices be "soft" (i.e., be laterally flexible or conformable), and thus atraumatic, to prevent rupturing of the delicate tissues of the aneurysm.

It is also advantageous that such vaso-occlusive devices be chronically retained within the aneurysm. However, aneurysms with larger mouths, commonly known as "wide neck aneurysms," present difficulty in the placement and retention of vaso-occlusive devices within the aneurysm sacs, particularly with small and relatively thin vaso-occlusive coils which lack the substantial secondary shape strength to maintain in position within such aneurysm sacs no matter how skillfully they are placed. For this reason, a stent or a balloon may be deployed in the vessel adjacent the neck region of the aneurysm to ensure that the vaso-occlusive coils are retained within the aneurysmal sac, thereby complicating the procedure. To address this particular issue, vaso-occlusive devices at least partially composed of a braided (or woven) structure have been developed. Such braided vaso-occlusive devices provide more coverage and a more effective backbone across the necks of aneurysms, and can thus be effectively retained within wide neck aneurysms without the need to deploy supplemental aneurysm-retaining devices, such as balloon or stents.

However, regardless of whether coiled or braided vaso-occlusive devices are used, vaso-occlusive device delivery systems may require that such vaso-occlusive devices be relatively short and limited in expandability, otherwise they are difficult (if not impossible) to push and/or retrieve to/from the microcatheter. Unfortunately, small (short) vaso-occlusive devices are less advantageous, since delivery of such small vaso-occlusive devices into an aneurysmal sac may require a longer and more involved procedure. For example, a 7 mm diameter neurological aneurysmal sac may typically be filled with five to seven individual spring shaped coils, resulting in a longer and more complicated procedure than if the number of devices was reduced.

Theoretically, the lengths of vaso-occlusive devices may be increased to reduce the number of such vaso-occlusive devices to treat an aneurysm. However, increasing the length of a vaso-occlusive device necessarily increases the friction of such vaso-occlusive device and the lumen of the delivery catheter. As such, the columnar strength of such vaso-occlusive device may be increased (e.g., by selecting a material with a high Young's modulus or increasing the diameter of the wire from which the vaso-occlusive device is formed) and/or the diameter of the delivery catheter may be increased to ensure that the vaso-occlusive device can be delivered into the aneurysm. However, as discussed above, it may be advantageous that both the diameter of the delivery catheter be as small as possible to allow the aneurysm to be accessed through a very small vasculature, and the vaso-occlusive device be soft enough to prevent trauma to the delicate tissues of the aneurysm.

Materials that enable a relatively long vaso-occlusive to have the suitable columnar strength to be delivered through a relatively small diameter delivery catheter, while satisfying the other countervailing design parameters, including softness, radiopacity, and MRI-compatibility, are very limited.

For example, known materials having a relatively high Young's modulus and relatively high radiopacity, such as platinum-tungsten (PtW) alloy from which vaso-occlusive coils are typically manufactured, can be used in an attempt to provide the suitable columnar strength for a relatively long vaso-occlusive device. However, the diameter of the wires from which such vaso-occlusive device is manufactured may be reduced to achieve certain softness while allowing the vaso-occlusive device to fit within a small diameter delivery catheter. As a result, the vaso-occlusive device would have a degraded radiopacity and a decreased columnar strength that would require a shortened vaso-occlusive device and/or larger diameter delivery catheter.

As another example, known materials having a relatively low Young's modulus and low radiopacity, such as nitinol, can be used in an attempt to provide the suitable softness for a vaso-occlusive device. However, such vaso-occlusive device would not have a suitable radiopacity and the columnar strength to increase the length of the vaso-occlusive device. Furthermore, the heating process used to set nitinol in its pre-determined shape results in a surface oxide that may crack and release toxic nickel. Thus, such oxide may be removed from the vaso-occlusive device using a costly and time-consuming process.

As still another example, known materials having a relatively medial Young's modulus and low radiopacity, such as titanium and the like, can be used in an attempt to provide the suitable columnar strength for a relatively long and soft vaso-occlusive device if an optimum diameter is selected for the wire from which such vaso-occlusive device is manufactured. However, such vaso-occlusive device would not exhibit the suitable radiopacity.

There, thus, is an ongoing need to provide a vaso-occlusive device that satisfies one or more of the foregoing design parameters.

SUMMARY

Embodiments described herein are directed to implantable medical devices, such as embolic devices and blood flow filters, that are at least partially made out of (i.e., composed of) gold-platinum-tungsten alloy.

In various embodiments, the implantable devices are made out of one or more elongate members composed of gold-platinum-tungsten alloy, such as in the form of a cut tube, a coiled wire, or a plurality of wires woven into a braid. Without limitation, the elongate members may include composite or non-composite wires having at least one layer, at least a core, or an entire cross-section, made out of the gold-platinum-tungsten alloy.

A vaso-occlusive device, includes: a vaso-occlusive structure configured for implantation in an aneurysm sac, the vaso-occlusive structure having a delivery configuration when restrained within a delivery catheter and having a deployed configuration when released from the delivery catheter into the aneurysmal sac, at least a portion of the vaso-occlusive structure being composed of a AuPtW (gold-platinum-tungsten) alloy; wherein the AuPtW alloy comprises platinum within a range 25%-40% by weight; and wherein the AuPtW alloy comprises tungsten within a range of 0.01%-10% by weight.

Optionally, the AuPtW alloy has a Young's modulus less than 25 mega-pounds per square inch (Mpsi).

Optionally, the vaso-occlusive structure comprises a mesh composed of the AuPtW alloy.

Optionally, the mesh is a braid.

Optionally, an entirety of the vaso-occlusive structure comprises the mesh.

Optionally, the vaso-occlusive structure further comprises two helically wound coils disposed at opposite ends of the mesh.

Optionally, each of the two helically wound coils is composed of the AuPtW alloy.

Optionally, the mesh comprises at least one wire, each having a minimum cross-sectional dimension in a range of 0.0005"-0.004".

Optionally, the mesh comprises at least one twisted strand.

Optionally, the mesh has a wire count in a range of 8-96 wires.

Optionally, the mesh has a wire count in a range of 16-32 wires.

Optionally, the mesh has an unconstrained braid angle in a range of 20 degrees to 60 degrees.

Optionally, the mesh has an expanded geometry having a circular cross-section.

Optionally, the mesh has an expanded geometry having a rectangular cross-section.

Optionally, the rectangular cross-section has a width in the range of 0.5 mm-5.0 mm.

Optionally, the mesh has a bending stiffness less than 150 mN/mm.

Optionally, the vaso-occlusive structure comprises a coil composed of the AuPtW alloy.

Optionally, the coil is configured to assume a three-dimensional shape having a plurality of loops when deployed out of the delivery catheter.

A vaso-occlusive assembly, includes: the vaso-occlusive device; and a pusher member to which the vaso-occlusive device is detachably coupled.

A vaso-occlusive treatment system, comprising: the vaso-occlusive assembly of claim; and the delivery catheter in which the vaso-occlusive assembly is disposed.

A vaso-occlusive device, includes: a vaso-occlusive structure configured for implantation in an aneurysm sac, the vaso-occlusive structure having a delivery configuration when restrained within a delivery catheter and having a deployed configuration when released from the delivery catheter into the aneurysmal sac, at least a portion of the vaso-occlusive structure being composed of a AuPtW (gold-platinum-tungsten) alloy.

Other and further aspects and features will become apparent from the ensuing detailed description in view of the accompanying figures.

DETAILED DESCRIPTION

Figures 1, 2:
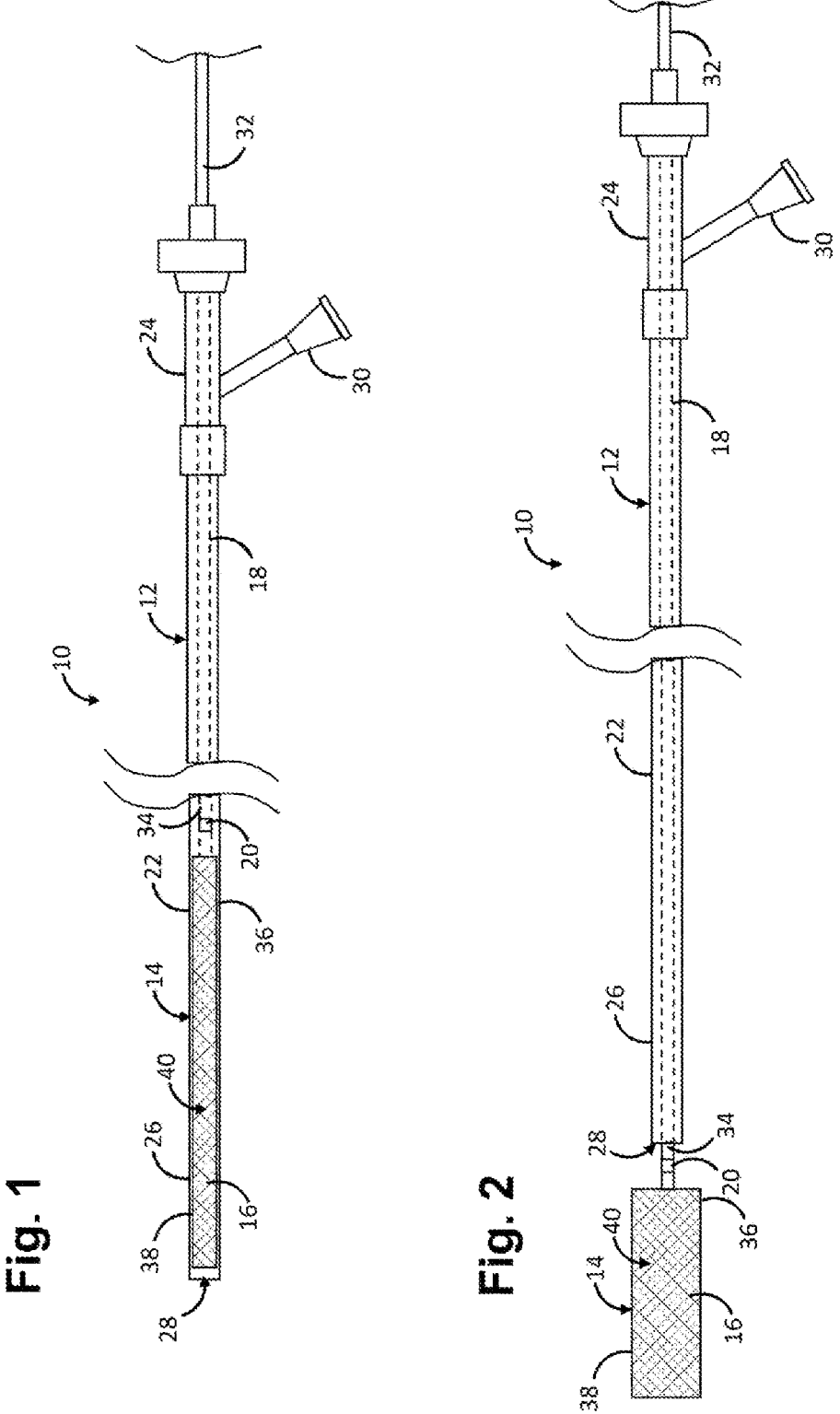
FIG. 1 is a side view of an vaso-occlusive treatment system, particularly showing the vaso-occlusive within the delivery catheter in a delivery configuration.
FIG. 2 is a side view of the vaso-occlusive treatment system of FIG. 1, particularly showing the vaso-occlusive device deployed from the delivery catheter in an expanded configuration.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various features are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are intended to facilitate the description of the features, and are not intended as an exhaustive description of the claimed inventions, or as a limitation on the scope thereof, which is defined by the appended claims and their equivalents.

In addition, the respective illustrated embodiments of the disclosed inventions need not have all of the depicted features, and a feature, aspect or advantage described in conjunction with a particular embodiment is not necessarily limited to that embodiment, but can be practiced in other embodiments, even if not so illustrated.

Referring to FIGS. 1 and 2, a vaso-occlusive treatment system 10 constructed in accordance with the present inventions will now be described. The vaso-occlusive treatment system 10 comprises a delivery catheter 12 and a vaso-occlusive assembly 14 slidably disposed within the delivery catheter 12. The vaso-occlusive assembly 14 comprises a vaso-occlusive structure 16 and a pusher member 18 to which the vaso-occlusive structure (or vaso-occlusive device) 16 is detachably coupled at a junction 20.

The delivery catheter 12 has a tubular configuration, and can, e.g., take the form of a micro-catheter or the like. The delivery catheter 12 comprises an elongate sheath body 22 having a proximal portion 24 and a distal portion 26, and a lumen 28 (shown in phantom) extending through the sheath body 22 between the proximal portion 24 and the distal portion 26. The proximal portion 24 of the sheath body 22 remains outside of the patient and accessible to the operator when the vaso-occlusive treatment system 10 is in use, while the distal portion 26 of the sheath body 22 is sized and dimensioned to reach remote locations of a vasculature and is configured to deliver the vaso-occlusive structure 16 to an aneurysm. The delivery catheter 12 may have at least one port 30 in fluid communication with the lumen 28 of the delivery catheter 12, which is used to introduce fluids into the sheath body 22. The vaso-occlusive assembly 14 is disposed in the lumen 28 of the delivery catheter 12, as better appreciated in FIG. 1.

The delivery catheter 12 may include one or more, or a plurality of regions along its length having different configurations and/or characteristics. For example, the distal portion 26 of the sheath body 22 may have an outer diameter less than the outer diameter of the proximal portion 24 of the sheath body 22 to reduce the profile of the distal portion 26 and facilitate navigation in tortuous vasculature. Furthermore, the distal portion 26 may be more flexible than the proximal portion 24. Generally, the proximal portion 24 may be formed from material that is stiffer than the distal portion 26 of the sheath body 22, so that the proximal portion 24 has a suitable pushability (e.g., the proximal portion 24 will not buckle or fold, etc.) to advance through the patient's vascular system, while the distal portion 26 may be formed of a more flexible material so that the distal portion 26 may remain flexible and track more easily over a guidewire to access remote locations in tortuous regions of the vasculature. The sheath body 22 may be composed of suitable polymeric materials, metals and/or alloys, such as polyethylene, stainless steel or other suitable biocompatible materials or combinations thereof. In some instances, the proximal portion 24 may include a reinforcement layer, such a braided layer or coiled layer to enhance the pushability of the sheath body 22. The sheath body 22 may include a transition region between the proximal portion 24 and the distal portion 26. In some cases, the distal portion 26 may also include a reinforcement layer.

In general, the vaso-occlusive structure 16 may be inserted into the patient by inserting (e.g., minimally invasively) the vaso-occlusive treatment system 10 into the patient's vasculature to reach the aneurysm site. The delivery catheter 12 is, thus, made as small as possible, and has an extremely narrow inner diameter (i.e., lumen 28) (e.g., between 0.015" and 0.025", and preferably between 0.015" and 0.018"). The vaso-occlusive treatment system 10 may be used in an "over-the-wire" configuration, wherein the delivery catheter 12 is introduced into the patient over a guidewire that has been previously introduced, and the delivery catheter 12 extends over the entire length of the guidewire (not shown). Alternatively, the vaso-occlusive treatment system 10 may be used in a "rapid-exchange" configuration, where a guidewire extends through a distal portion of the vaso-occlusive treatment system 10 from a guidewire port (not shown). In other alternative embodiments, the vaso-occlusive treatment system 10 may be introduced into the patient after a guidewire had been withdrawn leaving a sheath or access catheter distal portion at the target site for the vaso-occlusive treatment system 10 to navigate through the vasculature of the patient within the sheath or access catheter.

It should be noted that the delivery catheter 12 is not limited to have the examples of dimensions mentioned, and that the delivery catheter 12 may have other dimensions in other embodiments. For example, in other embodiments, the lumen of the delivery catheter 12 may have an internal diameter that is less than 0.020", less than 0.018", less than 0.016", or less than 0.014" (such as 0.013" or smaller). In other embodiments, the lumen of the delivery catheter 12 may have an internal diameter that is larger than 0.020", such as 0.04", 0.06", 0.08", 0.1", 0.2", etc.

As shown in FIGS. 1-2, when the vaso-occlusive structure 16 is contained inside the delivery catheter 12, the vaso-occlusive structure 16 has a first cross-sectional dimension, and when the vaso-occlusive structure 16 is delivered out of the delivery catheter 12, the vaso-occlusive structure 16 has a second cross-sectional dimension that is larger than the first cross-sectional dimension. In particular, when the vaso-occlusive structure 16 is inside the delivery catheter 12, the vaso-occlusive structure 16 elastically collapses radially to form the first cross-sectional dimension. When the vaso-occlusive structure 16 is outside the delivery catheter 12, the vaso-occlusive structure 16 elastically springs outward radially to assume its second cross-dimensional dimension. In some embodiments, in addition to expanding radially from a longitudinal axis of the vaso-occlusive structure 16, the vaso-occlusive structure 16 may also assume a three-dimensional configuration. By means of non-limiting examples, the vaso-occlusive structure 16 may assume a plurality of loops (e.g., open loops and/or closed loops), a spiral configuration, a random configuration, etc. In some embodiments, if the vaso-occlusive structure 16 assumes a three-dimensional configuration having a plurality of loops, the loops may lie within respective planes, and at least two planes may form a non-zero angle with respect to each other.

Figure 3:
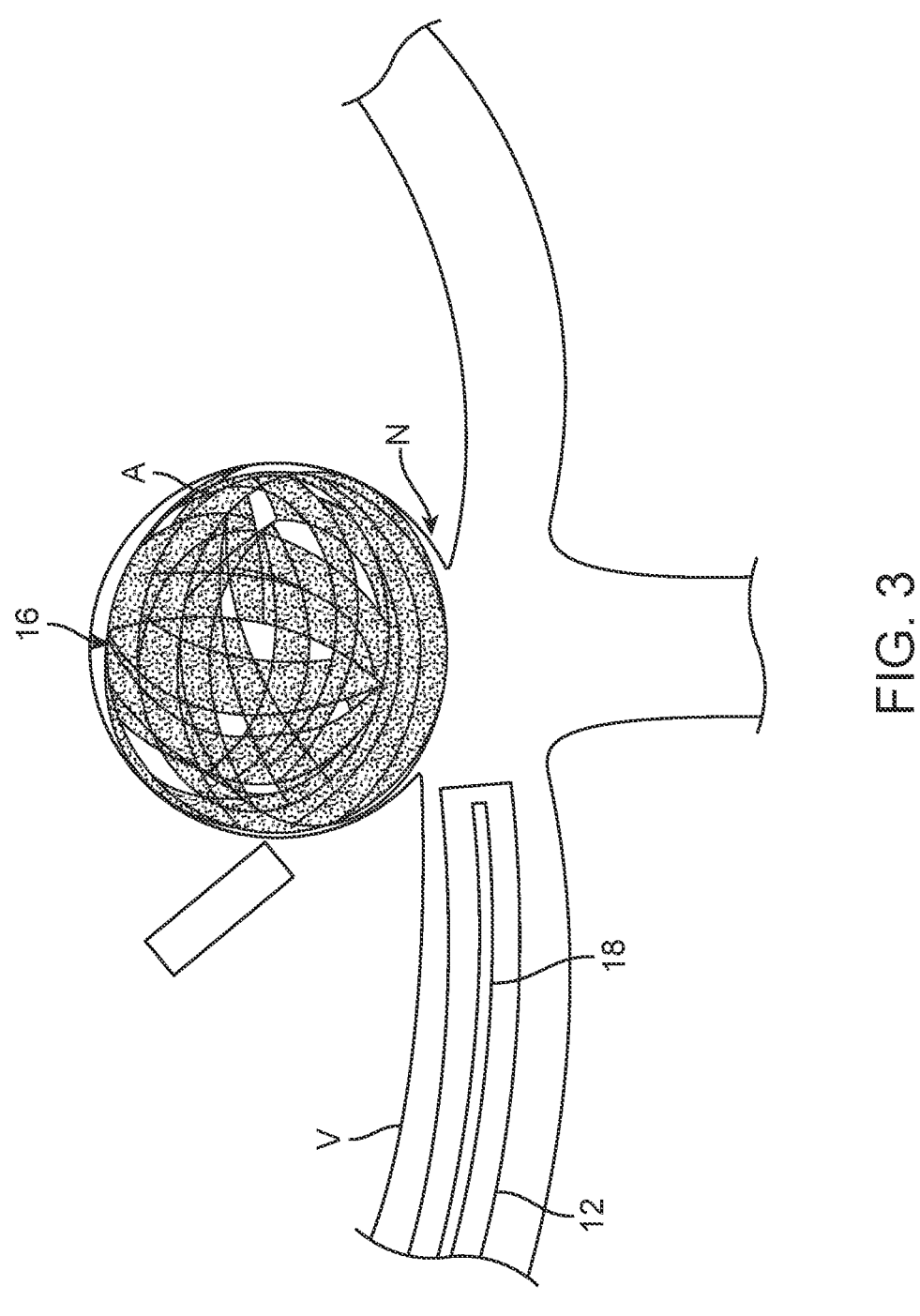
FIG. 3 is a plan view of a vaso-occlusive structure of the vaso-occlusive treatment system of FIG. 1, deployed within an aneurysmal sac.

As shown in FIG. 3, at the aneurysm site, the vaso-occlusive structure 16 may be pushed distally out of the delivery catheter 12 residing in the parent vessel V through the aneurysmal neck N and into an aneurysmal sac A via the pusher member 18. After being extruded from the delivery catheter 12, the vaso-occlusive structure 16 may self-expand into a pre-set configuration as described below. Once the vaso-occlusive structure 16 is inserted into the aneurysmal sac A, the vaso-occlusive structure 16 may be decoupled from the pusher member 18. A number of vaso-occlusive devices 16 may be delivered to fill and occlude the aneurysmal sac A. The vaso-occlusive structure 16 may also be removed or withdrawn, and collapsed back into the delivery catheter 12 by proximally withdrawing the vaso-occlusive structure 16 via the pusher member 18.

The pusher member 18 may be a coil, wire, tendon, or the like, having a suitable columnar strength to permit pushing of the vaso-occlusive structure 16 into the aneurysmal sac. The junction 20 at which the pusher member 18 is coupled to the vaso-occlusive structure 16 may, e.g., take the form of an electrolytically degradable segment for electrolytically decoupling the vaso-occlusive structure 16 from the pusher member 18, although other alternative detachment mechanisms for decoupling the vaso-occlusive structure 16 from the pusher member 18 may include mechanical, thermal, and hydraulic mechanisms.

The pusher member 18 has a proximal portion 32 that extends proximal from the proximal portion 24 of the delivery catheter 12 and a distal portion 34 to which the vaso-occlusive device 16 is attached. The pusher member 18 may be made of a guidewire, torqueable cable tube, or a hypotube. In either case, there are numerous materials that can be used for the pusher member 18 to achieve the suitable properties that are commonly associated with medical devices. Some examples can include metals, metal alloys, polymers, metal-polymer composites, and the like, or any other suitable material. For example, the pusher member 18 may include nickel-titanium alloy, stainless steel, a composite of nickel-titanium alloy and stainless steel. In some embodiments, at least a part (e.g., a layer), or an entirety, of the push member 18 may be made from nickel-titanium-platinum (NiTiPt) alloy. In some cases, the pusher member 18 can be made of the same material along its length, or in some embodiments, can include portions or sections made of different materials. In some embodiments, the material used to construct the pusher member 18 is chosen to impart varying flexibility and stiffness characteristics to different portions of the pusher member 18. For example, the proximal region and the distal portion 34 of the pusher member 18 may be formed of different materials, for example materials having different moduli of elasticity, resulting in a difference in flexibility. For example, the proximal portion 32 can be formed of stainless steel, and the distal portion 34 can be formed of a nickel-titanium alloy. However, any suitable material or combination of material may be used for the pusher member 18.

The vaso-occlusive structure 16 is sized for implantation in an aneurysmal sac A, which can take any geometry or shape in its cross-section. For example, in the illustrated embodiment, the vaso-occlusive structure 16 takes the form of a resilient tubular member having a proximal end 36 and a distal end 38. The distal end 38 of the vaso-occlusive structure 16, in this case, is typically free or loose (allowing maximal expansion) while the proximal end 36 of the vaso-occlusive structure 16 is coupled/attached to the pusher member 18. Thus, the distal end 38 of the vaso-occlusive structure 16 is free-floating. For another example, the vaso-occlusive structure 16 can take the form of flat member where both the proximal and distal ends can be fixed (minimal expansion is allowed). The vaso-occlusive structure 16 has a compact delivery configuration when radially restrained within the delivery catheter 12 and is biased to radially expand outward into a deployed configuration when released from the delivery catheter 12 into the aneurysmal sac. The cross-sectional dimension of the vaso-occlusive structure 16, in its expanded deployed configuration, may, e.g., be greater than 1.5 times, and preferably greater than 2 times, and most preferably, greater than 3 times, the cross-sectional dimension of the vaso-occlusive structure 16, in its compact delivery configuration. The expanded deployed configuration of the vaso-occlusive structure 16 may be pre-set and may be bent, curved, or three-dimensional (e.g., balled-up, looped, etc.), and may include a secondary or tertiary structure.

Figure 4:
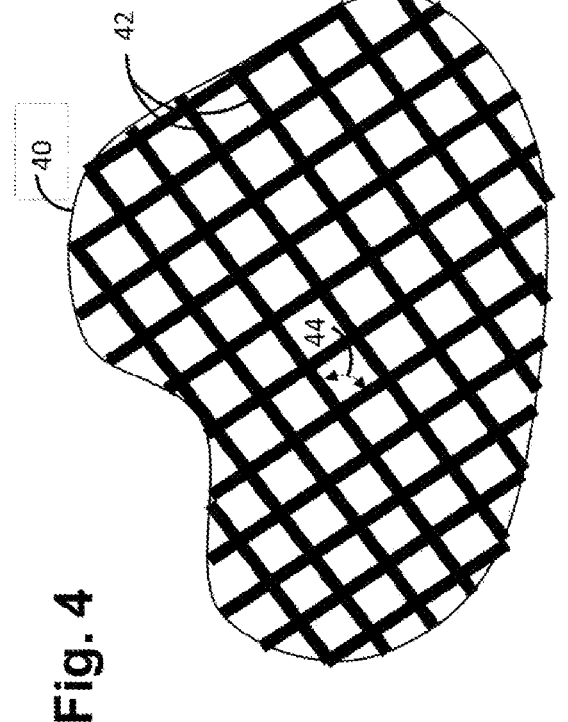
FIG. 4 is a plan view of a mesh portion of the vaso-occlusive structure of the vaso-occlusive treatment system of FIG. 1.

In the embodiment illustrated in FIGS. 1 and 2, the entirety of the vaso-occlusive structure 16 comprises a porous mesh 40 composed of the AuPtW alloy, although as will be discussed in further detail below, a portion of the vaso-occlusive structure 16 may comprise a mesh 40. In the illustrated embodiment, the mesh 40 is formed by braiding or weaving wires 42 (e.g., having a wire count in the range of 8-96 wires, and more preferably in the range of 16-32 wires) together (FIG. 4). In alternative embodiments, the mesh 40 may be formed as a monolithic structure, e.g., by etching or cutting a pattern from a tube or sheet of stent material, or by cutting or etching a sheet of material according to a designed pattern whereupon the sheet may be rolled or otherwise formed into the tubular, bifurcated or other shape.

The mesh 40 may have a suitable length (e.g., greater than 5 cm, between 5 cm and 45 cm, between 5 cm and 30 cm, etc). Braids may be formed using braiding machines, and may be braided around a mandrel (e.g., a mandrel having a round, oval, flat, other shape depending on the final cross-sectional shape of the vaso-occlusive structure 16 to be achieved). Alternatively, wires 42 may be woven into a flat braid and subsequently formed and heat set around a mandrel to a flat braid with a pre-determined shape. After braiding, the mesh 40 can be heat set (e.g., at 450 degree Celsius to 650 degree Celsius for 1 to 60 minutes). The heat set completed braid forms the linear "primary shape" of the mesh 40. The heat set completed braid can then be wrapped around a second mandrel (e.g., a three-dimensional mandrel) and heat set for a second time to impart a three-dimensional "secondary shape" or "tertiary shape."

Figure 5C:
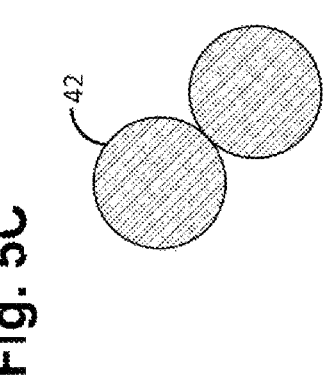
FIG. 5C is a cross-sectional view of a wire used in the mesh portion of FIG. 4.
Figure 5B:
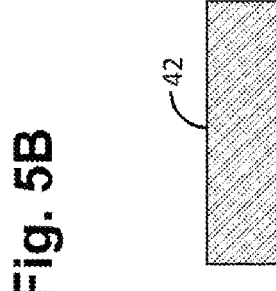
FIG. 5B is a cross-sectional view of a wire used in the mesh portion of FIG. 4.
Figure 5A:
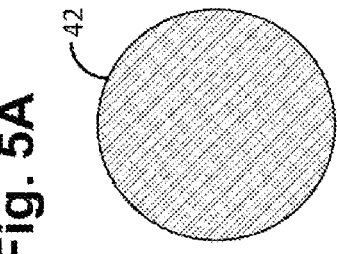
FIG. 5A is a cross-sectional view of a wire used in the mesh portion of FIG. 4.

Each wire 42 may be a monofilament strand, as illustrated in FIGS. 5A and 5B, although in alternative embodiments, each wire 42 may be a multi-filament strand, as illustrated in FIG. 5C. Each wire 42 may have any suitable cross-section with any suitable dimension. For example, if the cross-section of each wire 42 is circular (as illustrated in FIG. 5A), the diameter may be in the range of 0.0005"-0.0040", and if the cross-section of each wire 42 is rectangular (as illustrated in FIG. 5B), the thickness may be 0.0008" or thicker, and the width may be 0.005" or less. In another embodiment, each wire 42 may take the form of a twisted wire (as illustrated in FIG. 5C) to enhance the flexibility of the resulting vaso-occlusive structure 16.

Although all of the wires 42 from which the mesh 40 is composed may be of identical size and composition, it should be appreciated the wires 42 may have different sizes and composition, as long as at least some of the wires 42 making up the structure of the vaso-occlusive structure 16 are composed of AuPtW alloy. In some embodiments, the mesh 40 may be a braid, such as a ribbon braid. The braid may be made from wires of a same size, or wires with different sizes. In some embodiments, the braid may be made from wires having a same composition, or from wires with different compositions. Preferably, the mesh 40 has an unconstrained braid angle 44 (i.e., the angle between two crossing wires 42) in the range of 20 degrees to 130 degrees, more preferably in the range of 20 degrees to 60 degrees (FIG. 4). In general, a braid angle 44 can be the angle between two crossing wires 42 viewed long the direction of the longitudinal axis. Selecting the braid angle 44 may enhance pushability of the vaso-occlusive structure 16 within the delivery catheter 12 by preventing collapse of the mesh 40, which could otherwise result in bunching of the mesh 40 in the delivery catheter 12 when pushing and causing jamming of the vaso-occlusive structure 16 within the delivery catheter 12. Ultimately, the number of wires 42 in the mesh 40, the braid angle 44, and/or the expanded configuration relative to the collapsed configuration of the mesh 40 can be selected to optimally fit the inner diameter of the delivery catheter 12 used.

In some embodiments, the mesh 40 may be a braided structure have a tubular configuration. In other embodiments, the mesh 40 may have a non-tubular configuration. For example, in some embodiments, the mesh 40 may be a flat braid. A flat braid may be any braided structure with a cross-section having a width W and a thickness T (measured in a direction perpendicular to the width), wherein a ratio of W/T is equal to or greater than 2, 3, 4, 5, 6, 7, 8, 9, 10, 11, 12, 13, 14, 15, 16, 17, 18, 19, 20. Also, in some embodiments, the mesh 40 may be a ribbon braid. In one or more embodiments described herein, a braid may have a width that is anywhere from 0.020 inch (0.5 mm) to 0.197 inch (5 mm), and preferably anywhere from 0.030 inch (0.75 mm) to 0.079 inch (2.0 mm), and preferably anywhere from 0.030 inch (0.75 mm) to 0.06 inch (1.5 mm). In further embodiments, the braid may have a width that is 0.039 inch (1 mm) or larger. For example, in one implementation, the braid may have a width of about 1.25 mm (e.g., 1.25 mm+/−0.1 mm). In some embodiments, the braid may have a braid stiffness that is less than 150 mN/mm. Furthermore, in some embodiments, the braid may be formed from multiple braid wires 42 of the same size and/or same composition. In other embodiments, the braid may be formed from multiple braid wires 42 of different sizes and/or different compositions.

In some embodiments, when the braid is unconfined outside a catheter, the braid may have a first width, and when the braid is inside the catheter, it may elastically collapse and/or bend transversely (e.g., in a direction that is perpendicular to a longitudinal axis of the braid) to have a second width that is smaller than the first width. For example, the braid may be a flat braid that is curled or rolled up elastically to have the second width when inside the catheter, and may elastically spring into a relaxed configuration having the first width when deployed outside the catheter.

Figure 6B:
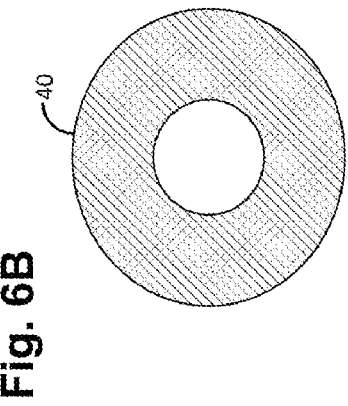
FIG. 6B is a cross-sectional view of the mesh portion of the vaso-occlusive treatment system of FIG. 1.
Figure 6A:
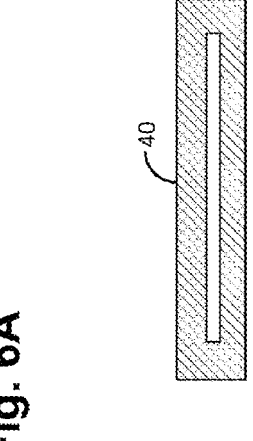
FIG. 6A is a cross-sectional view of the mesh portion of the vaso-occlusive treatment system of FIG. 1.

In one embodiment illustrated in FIG. 6A, the mesh 40 has an expanded geometry that is flat-shaped (e.g., a ribbon) and may, e.g., have a width in the range of 0.5 mm-5.0 mm. In an alternative embodiment illustrated in FIG. 6B, the mesh 40 may have an expanded geometry that is cylindrical (i.e., has a circular cross-section), and may, e.g., have a diameter in the range of 0.5 mm-5.0 mm. Thus, the mesh 40 may be a flat braid or a round braid. In some embodiments, regardless of whether the mesh 40 has a flat or rounded cross-section, the mesh 40 has a suitable column strength to be advanced relative to the delivery catheter 16 (e.g., the mesh 40 will not buckle, kink, fold, etc., inside the lumen of the delivery catheter 16 as it is being advanced).

Through prototyping and testing, the exact composition of the AuPtW alloy, size and number of wires 42, braid angle used to construct the mesh 40 of the vaso-occlusive structure 16, and shape and size of the expanded vaso-occlusive structure 16, can be optimized for superior performance, depending on the target application.

For example, in some embodiments, a relatively soft and long, but radiopaque, vaso-occlusive device may be constructed by braiding N (e.g., a number in the range of 8 to 96, and preferably 16 to 32, such as 24) wires at a braid angle (unconstrained) that is anywhere from 20-130 degrees (and preferably anywhere from 20-60 degrees) into a flat braid having a width of 0.5-5 mm (and preferably 1-2 mm, e.g., 1.25 mm) and a length of 12 cm or longer, with each wire being composed of AuPtW having a Young's modulus that is less than 25 Mpsi and having a wire diameter that is anywhere from 0.0005" to 0.004" (e.g., 0.001"). The vaso-occlusive may be deliverable through a microcatheter (e.g., having 0.026" outer diameter and 0.0165" inner diameter). In some embodiments, the vaso-occlusive device may be delivered with a frictional force less than 0.06 lbs. Such vaso-occlusive device may have an advantageous shape retention characteristic, a certain bending stiffness (e.g., less than 150 mN/mm), and certain radiopacity, such as imaging at x-ray energy of 82 kiloVoltage peak (KVp). Also, in some embodiments, MRI image (e.g., MRI at 3T) of the novel AuPtW vaso-occlusive coil may advantageously lack interfacial artifact that may be otherwise present in existing vaso-occlusive coils (e.g., vaso-occlusive coils made from Pt/8 W).

Significantly, the inventors have discovered that gold-platinum-tungsten (AuPtW) alloy, preferably comprising platinum within the range 25%-40% weight, tungsten within the range 0.01%-10% weight, balance Au (e.g., % of Au=100%-% of Pt-% of W), and a Young's modulus of less than 25×10^6 pounds per square inch (25 Mpsi), enables the vaso-occlusive structure 16, given a suitable structure, to exhibit certain softness (e.g., having a bending stiffness less than 150 mN/mm), to have a certain length (e.g., greater than 5 cm), to be compatible with a small diameter delivery catheter (e.g., 0.017" inner diameter), to have a certain radiopacity, to have a certain MRI compatibility, and ease of manufacture (e.g., no surface oxide removal). In other embodiments, in addition to an AuPtW alloy, the vaso-occlusive structure 16 may be further composed of iridium to improve its mechanical properties.

It should be noted that the vaso-occlusive structure 16 is not limited to having the examples of the dimensions and features described herein, and that the vaso-occlusive structure 16 may have various dimensions and features in different embodiments. For example, in some embodiments, the vaso-occlusive structure 16 may comprise a braided structure formed from braid wires 42. The braid wires 42 may have different shapes in different embodiments. For example, at least one of the braid wires 42 may have a circular cross section, a square cross section, an elliptical cross section, or a rectangular cross section, etc. In some embodiments, at least one of the braid wires 42 may have a cross-sectional dimension that is anywhere from 0.0001 inch (0.00254 mm) to 0.004 inch (0.1016 mm). In other embodiments, the braid wire 42 may have a cross-sectional dimension that is less than 0.00085 inch (0.022 mm), and preferably anywhere from 0.0001 inch (0.00254 mm) to 0.0008 inch (0.020 mm), and more preferably anywhere from 0.0003 inch (0.0076 mm) to 0.00075 inch (0.019 mm).

In some embodiments, if the braid wire 42 has a circular cross-section, the cross-sectional dimension described herein is the diameter of the circular cross-section. In such cases, the diameter may be in the range between 0.0005 inch (0.0127 mm) to 0.004 inch (0.102 mm), and preferably between 0.0008 inch (0.0203 mm) to 0.004 inch (0.102 mm), and more preferably, in the range between 0.001 inch (0.0254 mm) to 0.002 inch (0.051 mm). In other embodiments, the diameter of the circular cross-section of the braid wire 42 may be less than 0.00085 inch, and preferably between 0.0001 inch to 0.0008 inch, and more preferably between 0.0003 inch to 0.00075 inch. In further embodiments, the braid wire 42 may have a diameter that is anywhere from 0.0001 inch (0.00254 mm) to 0.0015 inch (0.0381 mm), and preferably anywhere from 0.0005 inch (0.0127 mm) to 0.001 inch (0.0254 mm).

Also, in some embodiments, a braid wire 42 may have an elongated cross-section (e.g., an oval shape, a rectangular shape, etc.) with a width W1 and height (or thickness) H1. In some embodiments, the width W1 may be 0.005" or less, and the height H1 may be at least 0.0008". In other embodiments, the braid wire 42 may have a width (W1) of 0.004 inch (0.102 mm) and a height (H1) of 0.002 inch (0.051 mm). In other embodiments, the braid wire 42 may have a maximum width of 0.002 inch (0.051 mm) and a minimum height of 0.0001 inch (0.00254 mm). In further embodiments, the braid wire 42 may have a cross-sectional dimension (width or thickness) that is less than 0.00085 inch.

In some embodiments, the braided structure may be formed from one or more twisted wire. In addition, in some embodiments, the braided structure may have a wire count that is anywhere from 8 to 96, anywhere from 16-32, anywhere from 24-144, or anywhere from 24-72. Also, in some embodiments, the braided structure may be formed by braid wires 42 that are ribbon wires.

Figure 7:
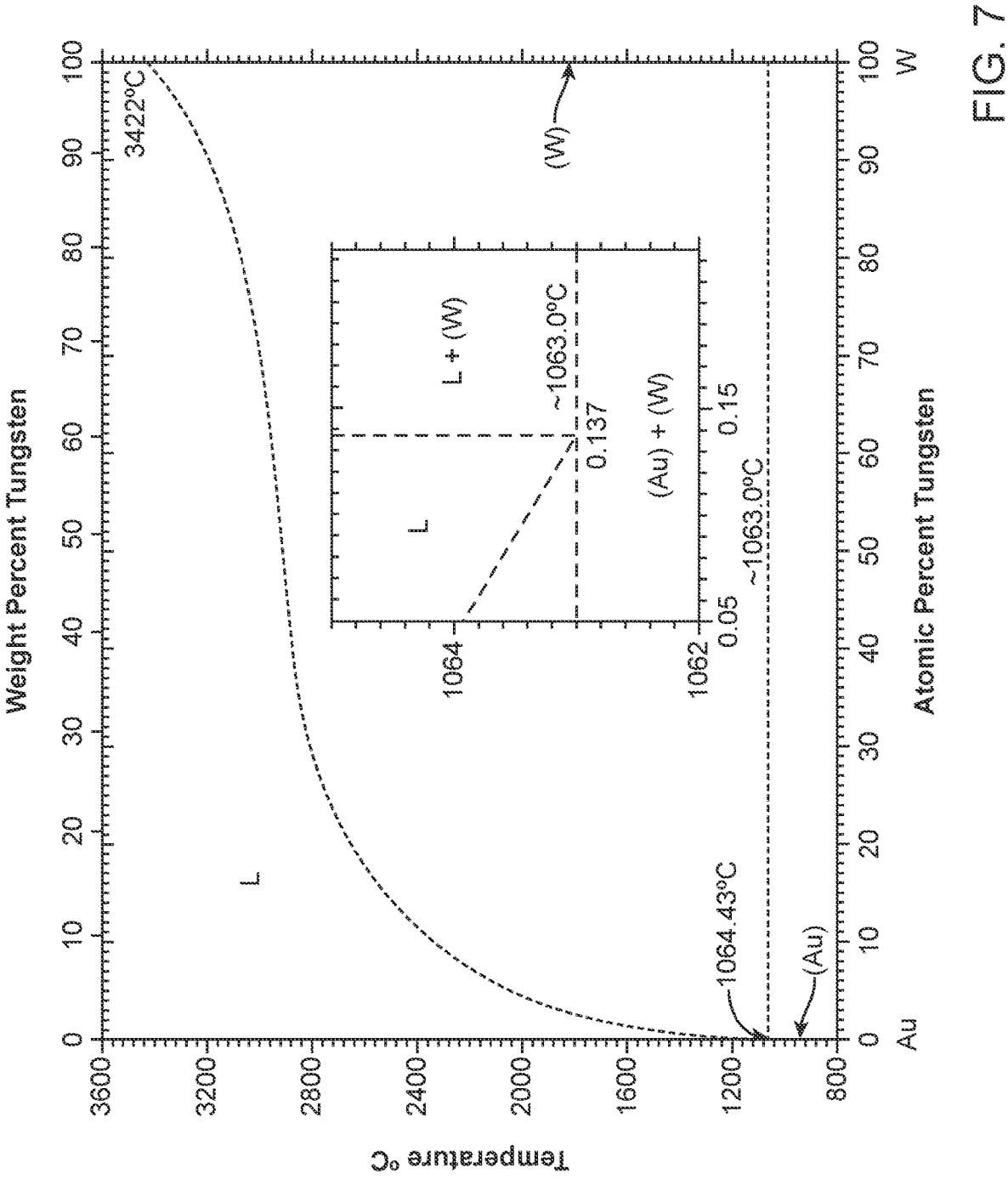
FIG. 7 illustrates an AuW phase diagram.

It should be noted that use of AuPtW alloy to construct a vaso-occlusive device is counter intuitive. This is because, it is believed that AuPt alloy cannot be strengthened through alloying with tungsten W. Au and W is a difficult combination to alloy for several reasons. First, tungsten has a much higher melting point (3422 degree Celsius) than gold (1064 degree Celsius) making it difficult to achieve a uniform solid solution and uniform chemical composition. Secondly, according to the AuW phase diagram (FIG. 7), Au and W appear to be immiscible in that they cannot form a single phase or unform solid solution at low temperatures. Also, tungsten has ultra-high hardness and high modulus, leading to the thinking that alloying using tungsten may result in an alloy that may be brittle. For these reasons, AuPtW alloy, especially AuPtW alloy in fine wire form, is currently not available commercially or academically. Also, for these same reasons, AuPtW alloy has not be used to construct implants, such as vaso-occlusive devices.

Nevertheless, the inventors discovered that a AuPtW ternary alloy with a uniform solid solution can be formed since AuPt and PtW when combined, can form an infinite solid solution with the platinum (Pt) acting as an inter-alloying element for gold (Au) and tungsten (W). Furthermore, through in-depth analysis and prototyping, the inventors also discovered that by controlling the tungsten content to less than 10% by weight, the AuPtW alloy possesses a set of mechanical properties that are suitable for making implants, such as vaso-occlusive devices. On the other hand, if the tungsten content exceeds 10% by weight in the AuPtW alloy, then the resulting alloy will be too brittle to be drawn into wire for braiding or for making coils, or too stiff for making implants.

In some embodiments, adding tungsten to the Au—Pt combination to make the alloy has the benefit of increasing the mechanical strength (ultimate tensile strength) to the range of 200 to 300 Kpsi as compared to 125 to 175 Kpsi for AuPt alloy without tungsten. However, tungsten itself has a very high modulus. Therefore, the content of tungsten is controlled to be 10% or less to achieve good mechanical strength while still maintaining a level of elastic modulus less than 25 Mpsi suitable for occlusive device applications.

In some embodiments, the vaso-occlusive structure 16 that is made from AuPtW alloy has the same or better softness, has the same or better radiopacity, has the same or longer braid length, compared to a vaso-occlusive structure made from AuPt alloy (without tungsten in the alloy).

Different techniques may be employed in different embodiments to make the AuPtW alloy. In one exemplary embodiment, solid PtW alloy and solid AuPt alloy may be obtained, and the alloys are then melted to obtain PtW solution and AuPt solution. The solutions may then be mixed to form AuPtW solution achieving the designed composition (e.g., 25-40% weight of Pt and 0.01-10% weight of W, balance Au, with respect to that of the designed AuPtW composition). In some embodiments, additional Au solution, Pt solution, W solution, or any combination of the foregoing, may optionally be added to the mixed solution to achieve the designed weight percentages of the respective ingredients (Au, Pt, W) in a fine tuning step.

In some embodiments, the alloy AuPt in solid form is first obtained. The AuPt alloy may be formed using an amount (e.g., 25-40% weight with respect to that of the designed AuPtW composition) of Pt. The AuPt alloy may then be heated to melt the alloy to obtain AuPt solution. Next, tungsten in solid form is obtained, and is melted to form tungsten solution. Then, an amount (e.g., less than 10% weight with respect to that of the designed AuPtW composition) of the melted tungsten solution is added to the AuPt solution to form AuPtW solution. In some embodiments, additional Au solution, Pt solution, W solution, or any combination of the foregoing, may optionally be added to the mixed solution to achieve the designed weight percentages of the respective ingredients (Au, Pt, W) in a fine tuning step.

In other embodiments, the alloy PtW in solid form is first obtained. The PtW alloy may be formed using an amount of Pt (e.g., 25-40% weight with respect to that of the designed AuPtW composition) and an amount (e.g., less then 10% weight with respect to that of the designed AuPtW composition) of W. The PtW alloy may then be heated to melt the alloy to obtain PtW solution. Next, Au in solid form is obtained, and is melted to form Au solution. Then, an amount of the melted Au solution is added to the PtW solution to form AuPtW solution. In some embodiments, additional Au solution, Pt solution, W solution, or any combination of the foregoing, may optionally be added to the mixed solution to achieve the designed weight percentages of the respective ingredients (Au, Pt, W) in a fine tuning step.

Also, in some embodiments, the vaso-occlusive device may have the AuPtW alloy that is at least: 50%, 60%, 70%, 80%, 90%, 95%, 97%, 98%, 99%, 99.5%, 99.9%, etc., in weight of the vaso-occlusive device. Moreover, as long as the percentage composition of tungsten (W) is equal to or less than 10% in weight of the AuPtW alloy, it should be appreciated that the percentage of gold (Au) and platinum (Pt) together in the alloy may be equal to 100%-Pw (wherein Pw represents percentage of W content in the AuPtW alloy), or may be less than 100%-Pw such that other materials may be present.

In some embodiments, the AuPtW material may further be alloyed with other material(s). For example, in other embodiments, AuPtW may be alloyed with tantalum (Ta), iridium (Ir), rhenium (Re), rhodium (Rh), ruthenium (Ru), molybdenum (Mo), or any combination of the foregoing, to obtain certain levels of mechanical properties (e.g., to enhance mechanical property of the material). In further embodiments, the material AuPtW may be further alloyed with Zr, Hf, or any combination of the foregoing, to reduce magnetic susceptibility.

Further, medical devices composed with the disclosed AuPtW alloy having a percentage of tungsten (W) that is equal to or less than 10% in weight of the alloy, may include one or more materials that impart certain properties to the device so as to withstand the manufacturing processes in producing the device. These manufacturing processes include, for example, laser cutting, etching, crimping, annealing, drawing, pilgering, electroplating, electro-polishing, chemical polishing, cleaning, pickling, ion beam deposition or implantation, sputter coating, vacuum deposition, or the like.

Using elongate members, such as braid wires, made from the AuPtW described herein to make implantable medical devices are advantageous. The combination of platinum, gold, and tungsten in the alloy AuPtW provides a suitable level of radiopacity, while the gold can also help achieve a certain level of magnetic susceptibility and tungsten can also help obtain a set of mechanical properties. In some applications where higher elastic modulus is more advantageous, more W can be added to the AuPtW alloy (the W content should still maintain less than 10% to avoid brittleness). In these applications, the higher Young's modulus (e.g., higher compared to AuPt without W content) of the AuPtW material allow implantable medical devices with higher axial (column) stiffness and strength to be made. As a result, the implantable medical devices may be even smaller in size (e.g., cross-sectional dimension) compared to previously known devices. One example of such implantable medical devices may be a vaso-occlusive device configured to be delivered to a small blood vessel to occlude an aneurysm. The small blood vessel may be any blood vessel in the body, including a distant blood vessel in a brain of a patient. Also, due to the higher mechanical strengths of the materials described herein, the implantable medical devices can be delivered smoothly using a small catheter without folding, buckling, and kinking. This is the case even if the medical device is made smaller in size. In addition, due to the higher ultimate tensile strength (UTS) of the materials, the elongate members forming the implantable medical devices will not easily be disrupted or break during handling and processing. Furthermore, because of the higher Young's modulus of the materials in these applications, smaller elongate members may be utilized to make implantable medical devices in order to achieve a softer bending stiffness. As a result, the implantable medical devices have a suitable bending stiffness and can exhibit better shape retention properties.

Properties of the disclosed gold-platinum-tungsten (AuPtW) alloy for making occlusive device can comprise one or more of the following exemplary properties, such as: suitable column strength for delivery, tensile strength, tensile elongation, stress-strain properties, radial force, radiopacity, flexibility, bendability, heat sensitivity, biocompatibility, and the like. Particularly, a medical device composed of AuPtW alloy with a percentage of tungsten (W) that is equal to or less than 10% in weight can have: greater radiopacity, radial strength, hardness, yield strength and/or ultimate tensile strength of the device; and/or may further improve stress-strain properties of the device, crimping and/or expansion properties, bendability and/or flexibility, overall strength and/or durability of the device, longitudinal lengthening properties, recoil properties, friction coefficient, heat sensitivity properties, biostability and/or biocompatibility properties. For example, a medical device composed of a percentage of tungsten (W) that is equal to or less than 10% of the AuPtW alloy, is configured to have a Young's modulus of less than 25 Mpsi. Additionally, or alternatively, medical devices composed of a percentage of tungsten (W) that is equal to or less than 10% of the AuPtW alloy are configured to have a magnetic susceptibility less than 300 ppm, preferably less than 200 ppm, more preferably less than 100 ppm resulting in reduced artifact during magnetic resonance (MR) imaging.

Figure 8A:
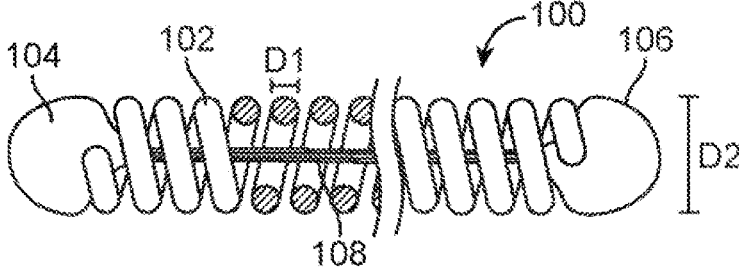
FIGS. 8A-8B illustrate another example of a vaso-occlusive device.
Figure 8B:
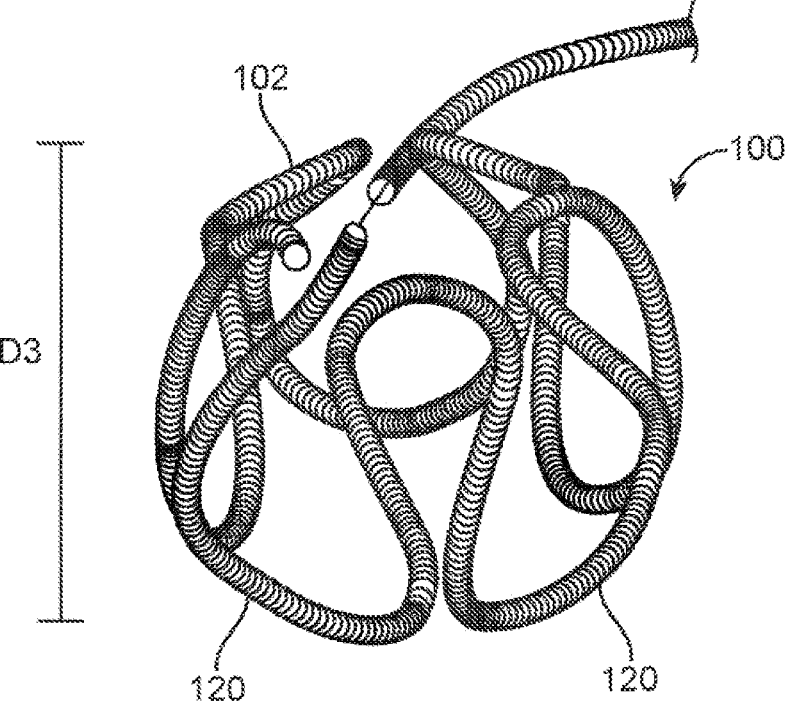

It should be noted that the vaso-occlusive structure 16 is not limited to having the examples of configurations described, and that the vaso-occlusive structure 16 may have other configurations in other embodiments. For example, in other embodiments, instead of the vaso-occlusive structure 16 having a mesh or a braid, the vaso-occlusive structure 16 may have a coil configuration. FIGS. 8A-8B illustrate an exemplary vaso-occlusive structure in the form of an embolic coil 100, constructed according to some embodiments. The coil 100 is formed of a helically wound wire 102 having a first end 104 and a second end 106. The wire 102 of coil 100 (FIGS. 8A-8B) is composed of the disclosed AuPtW alloy having a percentage of tungsten (W) that is equal to or less than 10% in weight. The coil 100 includes a stretch-resisting member 108 that is fixedly attached both to the first end 104 and to the second end 106. In alternative embodiments, the stretch-resisting member 108 may be attached to one of the two ends or to neither of the two ends. The coil 100 of FIG. 8A is shown in a "primary" winding or shape, and the coil 100 of FIG. 8B is shown in a "secondary" winding or shape. In some cases, the coil 100 has the primary winding or shape when restrained within a delivery catheter, and may assume the secondary winding or shape when deployed out of the delivery catheter. The secondary shape of the coil 100 of FIG. 8B forms a spherical three-dimensional shape having non-overlapping loops 120. It should be appreciated that secondary shape of the coil 100 may assume any other suitable shape. The wire 102 of coil 100 may be formed of a wire, drawn-filled tubes, threads, filaments or the like. In some embodiments, the wire 102 diameter (D1) ranges from about 0.0005 inch (0.0127 mm) to about 0.005 inch (0.127 mm), the primary wind diameter (D2) of the coil 100 ranges from about 0.003 inch (0.0762 mm) to about 0.030" (0.762 mm) and/or the secondary wind diameter (D3) ranges from about 0.5 mm to about 50 mm, as shown in FIGS. 8A-8B.

As previously disclosed, the coil 100 composed of the disclosed AuPtW alloy having a percentage of tungsten (W) that is equal to or less than 10% in weight, has lower MR artifact due to low magnetic susceptibility as compared to current vaso-occlusive devices.

As mentioned above, in some embodiments, an entirety of the vaso-occlusive structure 16 may have a braided construction (e.g., mesh 40), wherein one or more (e.g., all) of the wires in the braided construction is composed of AuPtW alloy. In other embodiments, the vaso-occlusive structure 16 may have at least one braid and at least one non-braid element. The non-braid element may be one or more coils. In some embodiments, the non-braid element may be composed of AuPtW alloy. In addition, in some embodiments, the braided construction or the braid may have one or more layer of braids (e.g., braid over braid). In other embodiments, the braided construction or the braid may be disposed over a coil to result in a braid-over-coil construction.

Figures 9, 10:
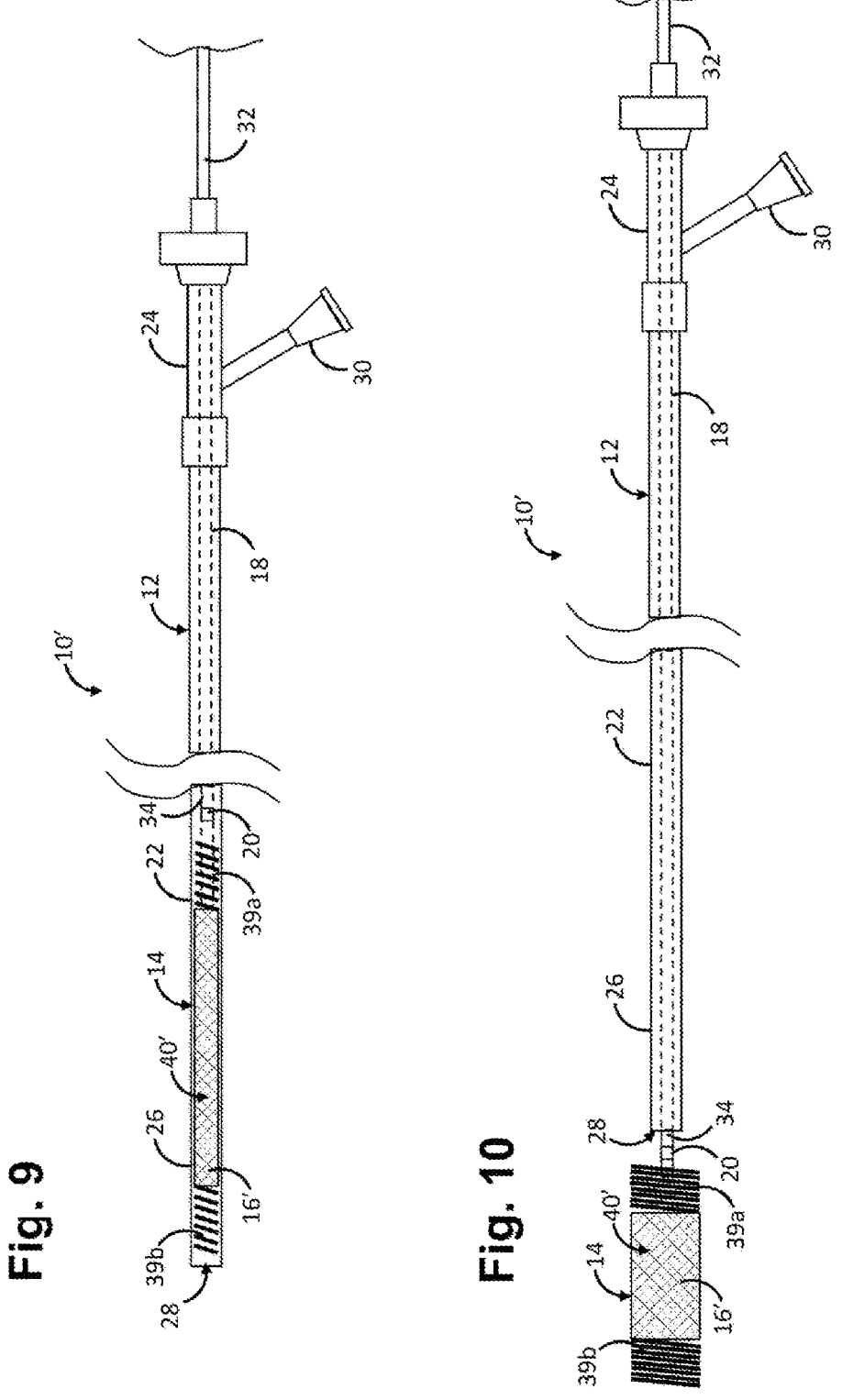
FIG. 9 is a side view of an vaso-occlusive treatment system, particularly showing the vaso-occlusive within the delivery catheter in a delivery configuration.
FIG. 10 is a side view of the vaso-occlusive treatment system of FIG. 9, particularly showing the vaso-occlusive device deployed from the delivery catheter in an expanded configuration.

For example, in other embodiments, the vaso-occlusive structure 16 may include with a mesh (or braid) and one or more coils. FIGS. 9 and 10 illustrate another embodiment of a vaso-occlusive treatment system 10' having a vaso-occlusive structure with a mesh 40' and coils 39a, 39b. In particular, the vaso-occlusive occlusive treatment system 10' is similar to the vaso-occlusive treatment system 10, with the exception that the vaso-occlusive structure 16' comprises a central mesh 40' and two helically wound coil 39a, 39b disposed at opposite ends of the central mesh 40'. The central mesh 40' can be constructed in the same manner as the mesh 40 described with respect to FIGS. 1 and 2. Preferably, the coil portions 39a, 39b are composed of a AuPtW alloy. Notably, the coil 39a, 39b provide additional non-traumatic characteristics to the vaso-occlusive structure 16'.

The coils 39a, 39b function as atraumatic members to prevent the vaso-occlusive structure 16' from puncturing or injuring tissue inside the patient. In some embodiments, the coil 39a/39b may comprise a coil wire having a cross-sectional dimension that is anywhere from 0.0001 inch (0.00254 mm) to 0.003 inch (0.075 mm), and wherein the coil 39a/39b has a primary wind diameter that is anywhere from 0.003 inch (0.076 mm) to 0.030 inch (0.762 mm). The coil 39a/39b forming the atraumatic member may have a simple or complex shape. In other embodiments, the vaso-occlusive structure 16' may not include both coils 39a, 39b, and may include the coil 39a or the coil 39b.

Although the vaso-occlusive structures 16, 16' respectively illustrated in FIGS. 1-2 and 9-10 have been described as having a single layer of braid, it should be appreciated the a vaso-occlusive structure may comprise multiple layers of braid (i.e., braid over braid construction), or may even comprise one braid layer (e.g., an outer layer of braid) and a coil layer (e.g., an inner coil) (i.e., a braid-over-coil construction). In either event, one or more layers (e.g., all layers) of the vaso-occlusive structure are preferably composed of a AuPtW alloy.

In some embodiments, implantable medical devices made from AuPtW alloy, such as the vaso-occlusive structure 16, described herein may have a length that is anywhere from 1.2 inch (3 cm) to 19.7 inch (50 cm), and preferably from 2 inch (5 cm) to 11.8 inch (30 cm). Also, in one or more embodiments, the implantable medical device (e.g., a braid) with any of the length described herein is considered as having a suitable column strength if the implantable medical device, when inserted lengthwise into an elongate lumen, can be pushed through the elongate lumen without buckling, kinking, or plastically deformed, wherein the elongate lumen has a maximum lumen width of 0.03 inch, and preferably a maximum width of 0.016 inch, and even more preferably a maximum width of 0.014 inch (e.g., 0.013 inch). The elongate lumen may be a lumen of a catheter, or any elongate lumen, such as a lumen of a tube that is for use to test the column strength of the implantable medical device.

It should be noted that the AuPtW alloy described herein should not be limited to make vaso-occlusive devices, and that the AuPtW alloy may be used to make other types of medical devices. For example, the disclosed AuPtW alloy having a percentage of tungsten (W) that is equal to or less than 10% in weight may be used to form devices such as: stents (e.g., slotted tube stents and/or braided or woven stents), filters, thromboembolic capture devices, flow diverters, intrasaccular aneurysm implants, vascular delivery assemblies, catheters, reinforcement members, guidewires, delivery wires, radiopaque markers and the like.

Also, in some embodiments, the implantable medical device described herein is considered as having a suitable shape retention property, if the implantable medical device with a certain initial radius R1 of curvature is inserted into a catheter, and has a radius R2 of curvature after the implantable medical device is deployed out of the catheter, wherein the radius R2 of curvature of the deployed implantable medical device is less than five times R1, or preferably less than four times R1, or more preferably less than 3 times R1, or even more preferably less than 2 times R1 (such as less than 1.5 times R1, or such as less than 1.2 time R1).

As used in this specification, the term "braid" refers to any structure formed by multiple elongate members, wherein the elongate members may or may not be woven to form the structure. In some embodiments, the braid may have a grid or mesh configuration with an open texture having spaced holes, wherein the spaced holes may form a certain uniform pattern, or may form a random pattern. In other embodiments, the braid may have other configurations, and may or may not have an open texture. In some embodiments, the elongate members may be coupled to each other by mechanical force, such as frictional force between the elongate members. By means of non-limiting examples, the frictional force coupling the elongate members to form the braid may be created by twisting the elongate members, weaving the elongate members, overlapping the elongate members, etc. In other embodiments, the elongate members may be coupled to each other by adhesive.

It should be noted that as used in this specification, the term "about" refers to a variation of a value that is within 10%, unless specifically stated otherwise. For example, equal to or less than "about 10%" by weight refers to a weight that is 10%+/−1% of the total weight or less.

Although particular embodiments have been shown and described herein, it will be understood by those skilled in the art that they are not intended to limit the disclosed inventions, and it will be obvious to those skilled in the art that various changes, permutations, and modifications may be made (e.g., the dimensions of various parts, combinations of parts) without departing from the scope of the disclosed inventions, which is to be defined by the following claims and their equivalents. The specification and drawings are, accordingly, to be regarded in an illustrative rather than restrictive sense. The various embodiments shown and described herein are intended to cover alternatives, modifications, and equivalents of the disclosed inventions, which may be included within the scope of the appended claims.

What is claimed is:

1. A vaso-occlusive device, comprising:
a vaso-occlusive structure configured for implantation in an aneurysm sac, the vaso-occlusive structure having a delivery configuration when restrained within a delivery catheter and having a deployed configuration when released from the delivery catheter into the aneurysm sac, at least a portion of the vaso-occlusive structure being composed of a AuPtW (gold-platinum-tungsten) alloy;
wherein the AuPtW alloy comprises Au having a weight WtAu, Pt having a weight WtPt, and W having a weight Wtw;
wherein a first ratio calculated as Wtpt/(WtAu+Wtpt+Wtw) is anywhere between 0.25 and 0.4; and
wherein a second ratio calculated as Wtw/(WtAu+Wtpt+Wtw) is less than 0.1.

2. The vaso-occlusive device of claim 1, wherein the AuPtW alloy has a Young's modulus of less than 25 Mpsi.

3. The vaso-occlusive device of claim 1, wherein the vaso-occlusive structure comprises a mesh composed of the AuPtW alloy.

4. The vaso-occlusive device of claim 3, wherein the mesh is a braid, and wherein the braid has a flat cross-sectional shape with a lumen.

5. The vaso-occlusive device of claim 3, wherein the vaso-occlusive structure further comprises two helically wound coils disposed at opposite ends of the mesh.

6. The vaso-occlusive device of claim 3, wherein the mesh comprises a wire, the wire having a minimum cross-sectional dimension in a range between 0.0005 inches and 0.004 inches.

7. The vaso-occlusive device of claim 3, wherein the mesh comprises at least one twisted strand.

8. The vaso-occlusive device of claim 3, wherein the mesh has a wire count in a range between 8 wires to 96 wires.

9. The vaso-occlusive device of claim 3, wherein the mesh comprises a plurality of wires, and wherein when the mesh is not constrained, at least two of the wires of the mesh cross each other at a braid angle in a range between 20 degrees and 60 degrees.

10. The vaso-occlusive device of claim 3, wherein the mesh comprises a rectangular or flat cross-section having a width in a range between 0.5 mm and 5.0 mm.

11. The vaso-occlusive device of claim 3, wherein the mesh has a bending stiffness less than 150 mN/mm.

12. The vaso-occlusive device of claim 1, wherein the vaso-occlusive structure comprises a coil composed of the AuPtW alloy.

13. The vaso-occlusive device of claim 12, wherein the coil is configured to assume a three-dimensional shape having a plurality of loops when in an unconstrained configuration.

14. A vaso-occlusive assembly, comprising the vaso-occlusive device of claim 1; and
a pusher member to which the vaso-occlusive device is detachably coupled.

15. A vaso-occlusive treatment system, comprising the vaso-occlusive assembly of claim 14; and
a delivery catheter in which the vaso-occlusive assembly is disposed.

16. The vaso-occlusive device of claim 1, wherein the vaso-occlusive structure comprises a flat braid with a first width, wherein the braid is curled or rolled up elastically to have a second width less than the first width when the vaso-occlusive structure is inside the delivery catheter.

17. The vaso-occlusive device of claim 1, wherein the AuPtW alloy is made from a PtW alloy.

18. The vaso-occlusive device of claim 1, wherein the vaso-occlusive structure has a magnetic susceptibility less than 300 ppm.

19. The vaso-occlusive device of claim 1, wherein the AuPtW alloy is at least 50% of a total weight of the vaso-occlusive device.

20. A vaso-occlusive treatment system comprising the vaso-occlusive device of claim 1 and a delivery catheter, wherein the vaso-occlusive device is inside the delivery catheter, and wherein a frictional force between the vaso-occlusive device and an inner surface of a wall of the delivery catheter is 0.06 lb or less.

* * * * *